US00PP34377P2

(12) United States Plant Patent
Verpaalen

(10) Patent No.: US PP34,377 P2
(45) Date of Patent: Jun. 28, 2022

(54) ***CORNUS* PLANT NAMED 'VERPAALEN2'**

(50) Latin Name: *Cornus alba*
Varietal Denomination: Verpaalen2

(71) Applicant: Henricus Cornelis E. M. Verpaalen, Zundert (NL)

(72) Inventor: Henricus Cornelis E. M. Verpaalen, Zundert (NL)

( * ) Notice: Subject to any disclaimer, the term of this patent is extended or adjusted under 35 U.S.C. 154(b) by 0 days.

(21) Appl. No.: 17/375,770

(22) Filed: Jul. 14, 2021

(51) Int. Cl.
*A01H 5/12* (2018.01)
*A01H 6/00* (2018.01)

(52) U.S. Cl.
USPC ..... Plt./220
CPC ..... *A01H 6/00* (2018.05)

(58) Field of Classification Search
USPC ..... Plt./220
CPC ..... A01H 6/00
See application file for complete search history.

(56) References Cited

PUBLICATIONS

UPOV hit on *Cornus* plant named 'Verpaalen02', QZ PBR 20202630, filed Oct. 26, 2020.*
CPVO application to PBR for a *Cornus* plant named 'Verpaalen02', PBR 20202630.*
PLUTO UPOV hit on *Cornus* plant named, 'Verpaalen2', QZ PBR 20202630, filed Oct. 20, 2020.*
PLUTO excerpt from UPOV hit on *Cornus* plant named, 'Verpaalen2', QZ PBR 20202630, filed Oct. 20, 2020, showing the denomination changes.*
CPVO Application Consultation for a UPOV hit on *Cornus* plant named, 'Verpaalen2', QZ PBR 20202630, filed Oct. 20, 2020.*

* cited by examiner

*Primary Examiner* — Anne Marie Grunberg
(74) *Attorney, Agent, or Firm* — Cassandra Bright

(57) ABSTRACT

A new and distinct cultivar of *Cornus* plant named 'VERPAALEN2' is disclosed, characterized by white-green variegated foliage edged in pink during Spring and Summer, and variegated pink and purple during late Summer into Winter. Plants are upright and broad. The new variety is a *Cornus*, normally used for outdoor ornamental purposes.

4 Drawing Sheets

Latin name of the genus and species: *Cornus alba.*
Variety denomination: 'VERPAALEN2'.

BACKGROUND OF THE INVENTION

The new variety is the result of a naturally occurring single-branch mutation of the unpatented *Cornus alba* 'Elegantissima'. *Cornus* 'Verpaalen2' was found and selected by the inventor in a field at a nursery in Zundert, The Netherlands, in October of 2015.

Asexual reproduction of the new cultivar was performed by vegetative cuttings. This was first performed at the same nursery in Zundert, The Netherlands, in Summer 2016, and has shown that the unique features of this cultivar are stable and reproduced true to type in multiple successive generations.

SUMMARY OF THE INVENTION

The cultivar 'VERPAALEN2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VERPAALEN2' These characteristics in combination distinguish 'VERPAALEN2' as a new and distinct *Cornus* cultivar:

1. White-green variegated leaves with pink edge in spring and early summer. Variegated intense pink-purple leaves in late summer into winter.
2. Red stems in autumn.

PARENT COMPARISON

Plants of the new cultivar *Cornus* 'VERPAALEN2' are similar to plants of *Cornus* 'Elegantissima' in most horticultural characteristics; however, plants of the new cultivar 'VERPAALEN2' differ in the following:

1. Leaves of 'Verpaalen2' are white-green variegated with a pink edge, while 'Elegantissima' has green leaves with white margins, occasionally light pink.

COMMERCIAL COMPARISON

Plants of the new cultivar 'VERPAALEN2' are comparable to the commercial variety *Cornus* 'Ivory Halo', unpatented. The two *Cornus* varieties are similar in most horticultural characteristics, however, the new variety 'VERPAALEN2' differs in the following:

1. Leaves of 'Verpaalen2' are white-green variegated with a pink edge, while 'Ivory Halo' has green leaves with white margins.

Plants of the new cultivar 'VERPAALEN2' are comparable to the commercial variety *Cornus* 'Cream Cracker', U.S. Plant Pat. No. 12,830. The two *Cornus* varieties are similar in most horticultural characteristics; however, the new variety 'VERPAALEN2' differs in the following:

1. The new variety has white flowers, while this comparator has yellow-green flowers tinged with pink.
2. The new variety has lighter green foliage than this comparator.

BRIEF DESCRIPTION OF THE PHOTOGRAPHS

The accompanying photographs illustrates various views of the new variety as well as a comparison with a comparator variety. The photographs were taken using conventional techniques and although colors may appear different from actual colors due to light reflectance it is as accurate as possible by conventional photographic techniques.

Figure 1:
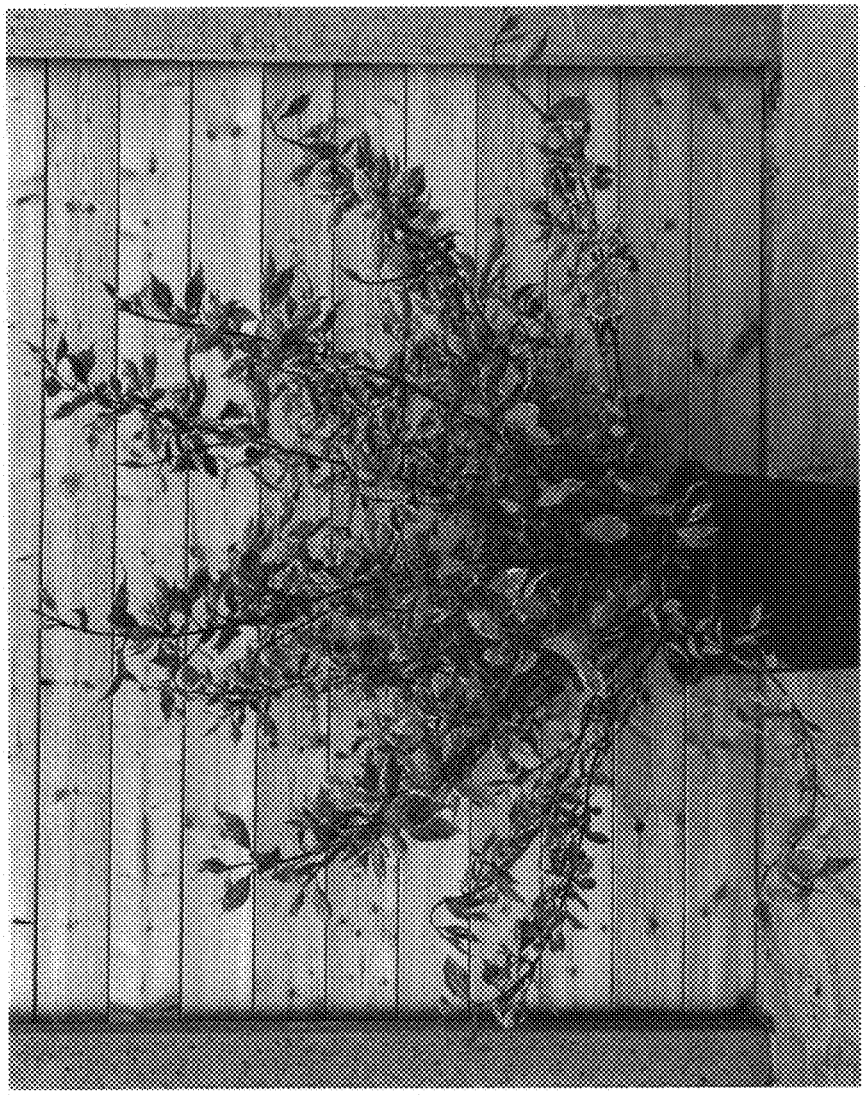
FIG. 1 illustrates a plant of the new variety at approximately 2 years old.
Figure 2:
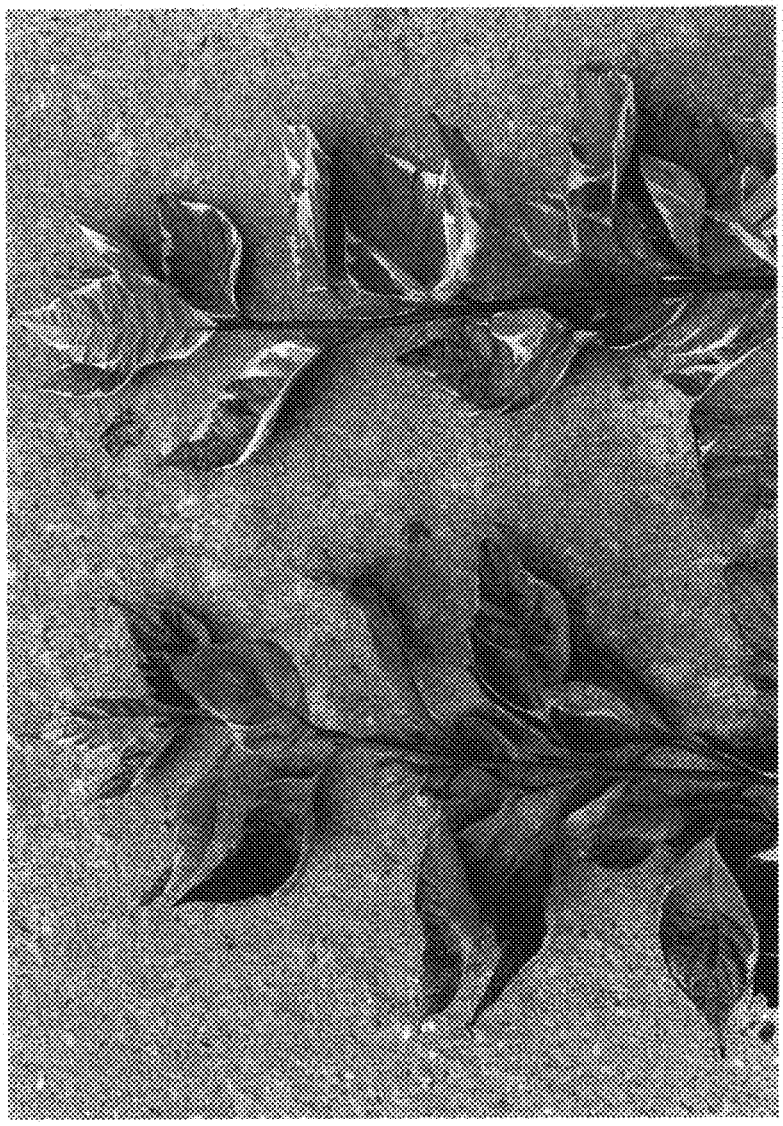
FIG. 2 illustrates a comparison with the parent variety. On the left of the photograph is a stem of the new variety, on the right a stem of the parent variety.
Figure 3:
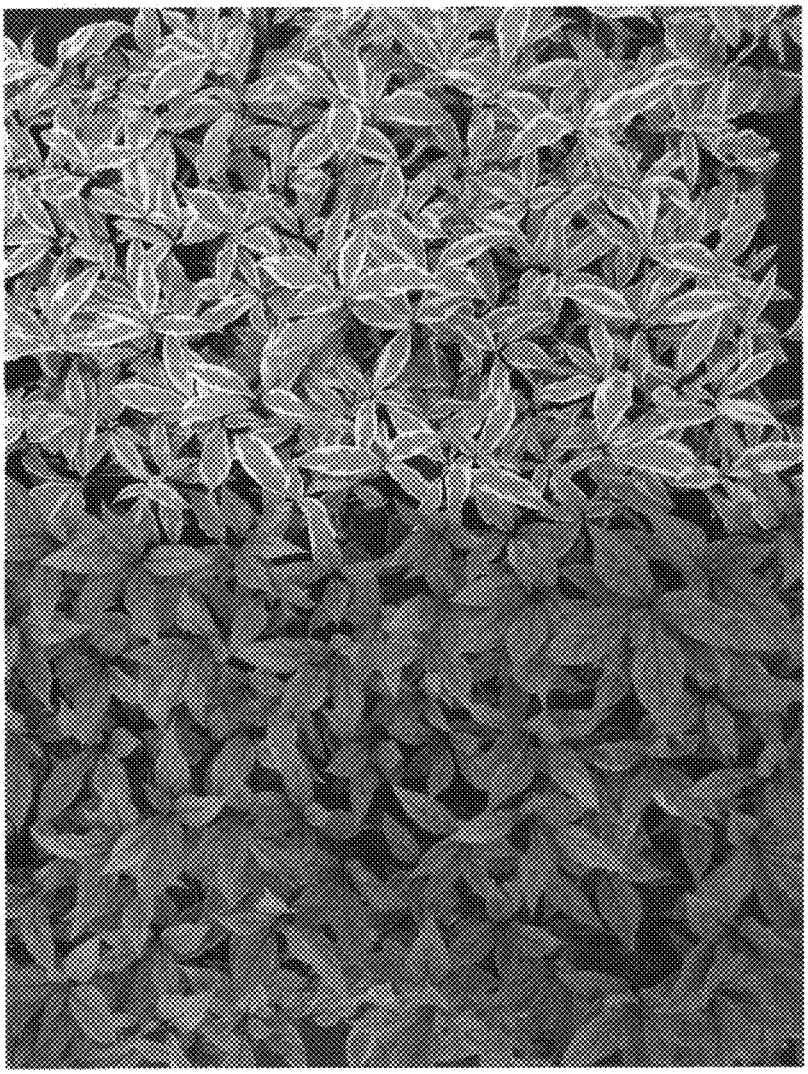

FIG. 3 is another comparison with the parent variety. The photograph is of liner trays, taken during Fall. The pink foliage on the left is of the new variety; on the right is the parent variety.

Figure 4:
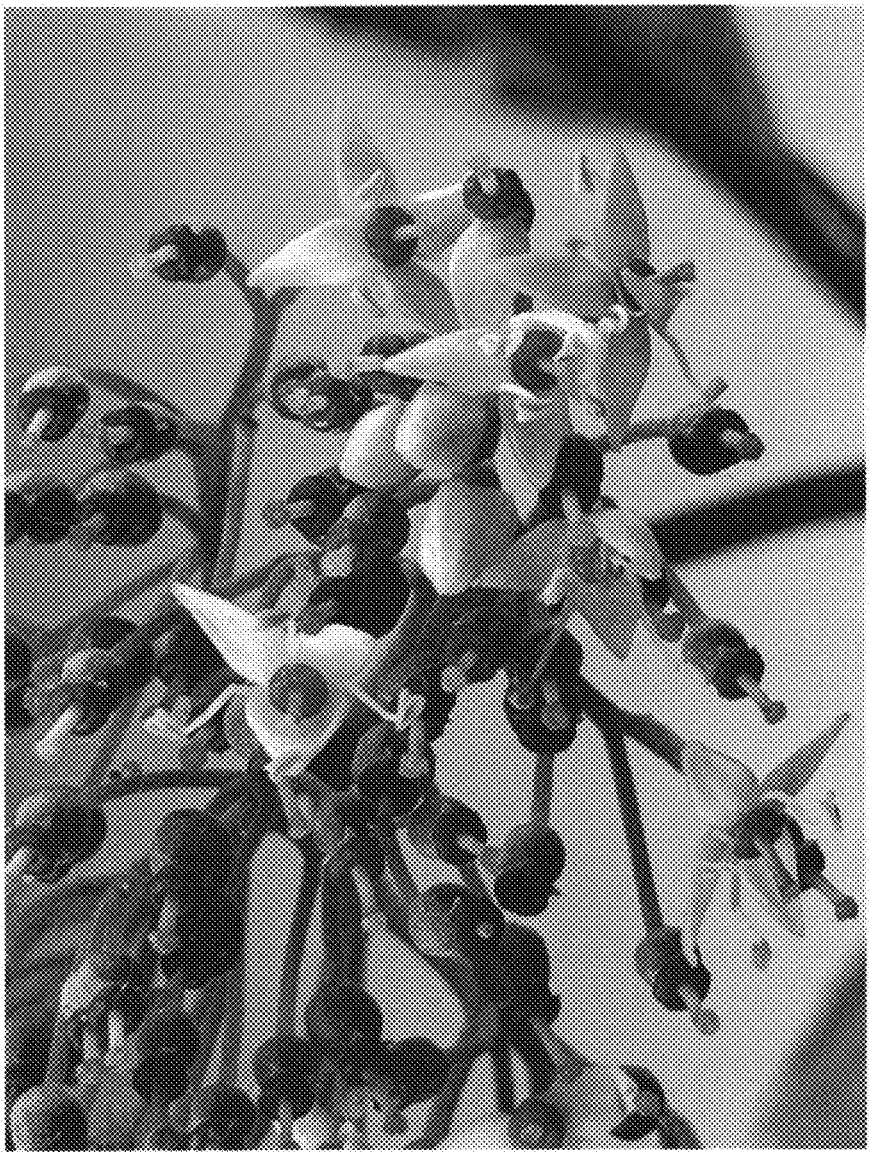

FIG. 4 illustrates flowers of the new variety.

DETAILED BOTANICAL DESCRIPTION

In the following description, color references are made to The Royal Horticultural Society Colour Chart 6$^{th}$ Edition 2015 except where general terms of ordinary dictionary significance are used. The following observations and measurements describe 'VERPAALEN2' plants grown outdoors in Zundert, the Netherlands. The growing temperature ranged from approximately 8° C. to 32° C. during the day and from approximately 1° C. to 12° C. during the night. General light conditions are normal sunlight and numerical values represent averages of typical plant types. Measurements were taken during June of 2020.

Botanical classification: *Cornus alba* 'VERPAALEN2'.

PROPAGATION

Type of propagation typically used: Terminal vegetative cuttings.
Time to initiate roots: 4 weeks.
Time to produce a rooted cutting: 4 months to a 9 cm pot.
Root description: Very thin, fibrous, not fleshy, freely branching. New roots colored near RHS Yellow-White 158D. Older roots colored near Grey-Brown 199D.

PLANT

Age of plant described: 2 to 3 years old from a rooted cutting.
Container size: 3-gallon container.
Plant type: Deciduous shrub.
Growth habit: Upright, broad.
Plant spread: 130 cm.
Plant height: 100 cm.
Growth rate: Moderate to vigorous.
Stem:
- *Main basal branches*.—Quantity: 10. Length: 88 cm. Diameter: 5 cm.
- *Lateral branches*.—Quantity: 6 per basal stem. Length: 53 cm. Diameter: 5 cm.
- *Color*.—New Growth: RHS Purple-Brown 183A. Old Growth: RHS Purple-Brown 166A.
- *Shape*.—Oval.
- *Pubescence*.—Very sparsely covered with short, pale grey hairs.
- *Other*.—Stems have light brown lenticels less than 1 mm in length.

Internode length: Average 5 cm.

FOLIAGE

Leaf:
- *Arrangement*.—Opposite.
- *Division*.—Simple.
- *Average length*.—Up to 9 cm.
- *Average width*.—Up to 3.5 cm.
- *Shape of blade*.—Elliptic.
- *Apex*.—Acuminate.
- *Base*.—Cuneate.
- *Margin*.—Entire.
- *Texture of top surface*.—Slightly pubescent.
- *Color*.—Young foliage upper side: RHS Brown N199A, with hints of Green 137C. Margins Purple-Red 185B. Young foliage under side: RHS Greyed-Green 197B, with hints of Green 137C. Margins Purple-Red 185B. Mature foliage upper side: RHS Green 137A, margins White 155A, with Purple-Red 185B. Mature foliage under side: RHS Green 137C, margins White 155A, with Purple-Red 185B.
- *Venation*.—Type: Pinnate. Venation color upper side: Near RHS Purple-Brown 183A. Venation color under side: Near RHS Purple-Brown 166A.
- *Petiole*.—Length: Up to 1.8 cm. Diameter: About 1.5 mm. Color: RHS Purple-Brown 183A.

FLOWER

Natural flowering season: Early Summer.
Arrangement: Compound corymb.
Quantity per lateral stem: About 150 flowers per inflorescence.
Quantity per plant: 3 inflorescences.
Inflorescence size:
- *Width*.—About 5 cm.
- *Length*.—About 2.2 cm.

Individual flowers:
- *Type*.—Single.
- *Diameter*.—About 7 mm.
- *Depth*.—About 4 mm.
- *Persistence*.—Self-cleaning.
- *Fragrance*.—None.

Petals:
- *Arrangement*.—Cross.
- *Number*.—4.
- *Shape*.—Ovate.
- *Margin*.—Entire.
- *Apex*.—Acute.
- *Base*.—Truncate.
- *Length*.—About 4 mm.
- *Width*.—About 2 mm.
- *Texture*.—Smooth.
- *Color*.—When opening: RHS White 155A. Fully opened: RHS White 155A.

Bud:
- *Shape*.—Ovoid.
- *Length*.—About 3 mm.
- *Diameter*.—About 2.5 mm.
- *Color*.—RHS White 155A.

Calyx:
*Shape*.—Campanulate.
*Length*.—About 2 mm.
*Diameter*.—About 2 mm.
*Color*.—Near RHS Green 138B.
Sepals:
*Arrangement*.—Fused to calyx.
*Margin*.—Entire.
Peduncle:
*Length*.—About 0.8 cm; secondary peduncle 0.6 cm.
*Diameter*.—About 2 mm; secondary peduncle 1 mm.
*Texture*.—Slightly pubescent.
*Color*.—RHS Green 146C, with hints of Purple-Brown 183A.
*Strength*.—Strong.
Pedicel:
*Length*.—About 0.8 cm.
*Diameter*.—Less than 1 mm.
*Texture*.—Slightly pubescent.
*Color*.—RHS Green 146C, with hints of Purple-Brown 183A.

REPRODUCTIVE ORGANS

Stamens:
*Number*.—4.
*Filament length*.—About 5 mm.
*Filament color*.—Near RHS White 155A.
Anthers:
*Shape*.—Oblong.
*Length*.—About 0.1 mm.
*Color*.—Near RHS Yellow-White 158D.
*Pollen*.—Scant.
*Color*.—Near White N155C.
Pistil:
*Number*.—1.
*Length*.—About 1.5 mm.
*Color*.—Near RHS Red 49D.
Stigma:
*Shape*.—Globular.
*Color*.—RHS Purple-Red 185B.
Ovary:
*Shape*.—Globular.
*Diameter*.—About 3 mm.
*Color*.—Near RHS Yellow-Green 145D.

OTHER CHARACTERISTICS

Fruits and seeds: Drupe, occurring late Summer. About 3 to 4 mm in diameter, colored near Green 138B.
Disease/pest resistance: Neither resistance nor susceptibility to other normal diseases and pests of *Cornus* observed.
Temperature range: USDA Zones 3-7.

What is claimed is:

1. A new and distinct cultivar of *Cornus* plant named 'VERPAALEN2' as herein illustrated and described.

* * * * *